United States Patent [19]

Hatamoto et al.

[11] Patent Number: 5,665,584
[45] Date of Patent: Sep. 9, 1997

[54] DNA FRAGMENT CONTAINING A TANNASE GENE, A RECOMBINANT PLASMID, A PROCESS FOR PRODUCING TANNASE, AND A PROMOTER

[75] Inventors: Osamu Hatamoto; Teruo Watarai; Kiyoshi Mizusawa; Eiichi Nakano, all of Noda, Japan

[73] Assignees: Noda Institute For Scientific Research; Kikkoman Corporation, both of Noda, Japan

[21] Appl. No.: 460,860

[22] Filed: Jun. 5, 1995

[30] Foreign Application Priority Data

Jul. 12, 1994 [JP] Japan .................. 6-159973
Apr. 10, 1995 [JP] Japan .................. 7-083973

[51] Int. Cl.⁶ .................. C12N 9/18; C12N 15/00; C07H 21/04
[52] U.S. Cl. .................. 435/197; 435/320.1; 536/23.2; 536/24.1
[58] Field of Search .................. 435/197, 320.1; 536/23.2, 24.1

[56] References Cited

U.S. PATENT DOCUMENTS 3,812,266   5/1974   Sanderson et al. .................. 426/52
4,426,448   1/1984   Okamura et al. .................. 435/146

FOREIGN PATENT DOCUMENTS 0 307 071   3/1989   European Pat. Off. .

*Primary Examiner*—Robert A. Wax
*Assistant Examiner*—Lisa J. Hobbs
*Attorney, Agent, or Firm*—Oblon, Spivak, McClelland, Maier & Neustadt, P.C.

[57] ABSTRACT

The present invention relates to a DNA fragment of 3,563 base pairs containing a gene coding for tannase and derived from a microorganism belonging to the genus Aspergillus, with the following restriction enzyme map:

B: Bam HI, H: Hind III, K: Kpn I, S: Sal I, X: Xba I; a DNA fragment containing a tannase gene coding for the amino acid sequence of (SEQ ID NO:4); a recombinant plasmid comprising the DNA fragment containing the tannase gene inserted into a plasmid vector; a process for producing tannase, comprising culturing a microorganism belonging to the genus Aspergillus capable of producing tannase in medium with the recombinant plasmid, and recovering tannase from the culture; and a promoter represented by the nucleotide sequence of (SEQ ID NO:1). Tannase can be efficiently produced according to the present invention.

6 Claims, 1 Drawing Sheet

B: Bam HI, H: Hind III, K: Kpn I, S: Sal I, X: Xba I

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 967 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
GAAGTCTAGT  CAGGGGGAGC  CGGGTATATA  CTCTTCCGTA  ACTCTGAGTA  TAATGTTTGG   60
TACTCGTCAA  TTGTCCCTAT  CGTTCGTTGT  TCAAATGTTG  AACGACCTTC  GTTAACAGTC  120
CATAATCGGT  TGCCCTGTTC  TGTAAACGTA  TTTGGGAGCC  GCTCAGCATT  TTCCGCCTTG  180
GTATAGGTCT  TCTTGTTGTA  GGTATACAAT  GCTACGATGT  TGAGGCTGAT  GGTACCTGAT  240
GCTCGGAGAT  AAAAAATTAA  ACACAACACG  TTAGGTAACG  TTTGATGCAA  TTTGCCCCTG  300
ATCAACGATT  GGAACTGGAG  GTGATTGGAG  ACCAAATTCT  TCAGCATCTT  ATCTTTGATT  360
GTTAACTCCG  AGGGCTCGGG  AATAGTTACC  CGTTTCCTCT  TAGCGGATGC  AATAGAGCAA  420
GAAAACGTGC  CAAAATACTC  AAGAAAGACC  GCGTCAGACA  AGATGAGTGC  CAAGAGAGAG  480
CCAAATCTCG  GTCATTGTAT  CTCCCTTGAA  TGTTGCTGAC  ATGGTGGCTC  GATCATGGAT  540
AGCTTTGCAC  GCGCAAGGGT  CAGGGCTGCA  TGGAGAGATC  AGATAAGGCC  GGATCTCAGC  600
CGAACCGGAA  CATCAGATAA  CAAAAATTCA  TCGTCGGACG  ACCGGAGACT  ACTACTACTA  660
CTAGTATCAA  CTCCGCGGGT  CGAGCCTCGA  GGAAGACCTT  TTGACTTGGC  ATCTTGCCAC  720
```

```
GCAACCCGGT GACGACAGCC TGAGTAGAAT TAAGGATGGC AAAGCGTTGA TCTGCCGTTT        780

GGTCCACAAG CTTGTTACGA ATCCCGAACC TTATGATGCC GAAGACGGTG GTCTCTCAGC        840

CCTAGCCTTG CAATAAATAG GACGATAGTT TCCCTATGGC TCCTCCTAGA TACGACCTCA        900

TCATTCGTTT ATTCCTTTCG TATCCTTTGA ACACTCCTTG ACCTCTGCCA TTCTTTTGGT        960

TCGAAAG                                                                  967
```

( 2 ) INFORMATION FOR SEQ ID NO:2:

( i ) SEQUENCE CHARACTERISTICS:
        ( A ) LENGTH: 16 amino acids
        ( B ) TYPE: amino acid
        ( C ) STRANDEDNESS: double
        ( D ) TOPOLOGY: linear ( i i ) MOLECULE TYPE: peptide ( x i ) SEQUENCE DESCRIPTION: SEQ ID NO:2:

```
Pro Ser Ile Pro Ala Ala Ser Ser Val His Tyr Trp Gln Ala Val Arg
 1               5                  10                  15
```

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( C ) STRANDEDNESS: double
        ( D ) TOPOLOGY: linear ( i i ) MOLECULE TYPE: peptide ( x i ) SEQUENCE DESCRIPTION: SEQ ID NO:3:

```
Ala Ser Phe Thr Asp Val Cys Thr Val Ser Asn Val Lys Ala Ala Leu
 1               5                  10                  15
```

( 2 ) INFORMATION FOR SEQ ID NO:4:

( i ) SEQUENCE CHARACTERISTICS:
        ( A ) LENGTH: 588 amino acids
        ( B ) TYPE: amino acid
        ( C ) STRANDEDNESS: double
        ( D ) TOPOLOGY: linear ( i i ) MOLECULE TYPE: protein ( x i ) SEQUENCE DESCRIPTION: SEQ ID NO:4:

```
Met Arg Gln His Ser Arg Met Ala Val Ala Ala Leu Ala Ala Gly Ala
 1               5                  10                  15

Asn Ala Ala Ser Phe Thr Asp Val Cys Thr Val Ser Asn Val Lys Ala
                20                  25                  30

Ala Leu Pro Ala Asn Gly Thr Leu Leu Gly Ile Ser Met Leu Pro Ser
                35                  40                  45

Ala Val Thr Ala Asn Pro Leu Tyr Asn Gln Ser Ala Gly Met Gly Ser
            50                  55                  60

Thr Thr Thr Tyr Asp Tyr Cys Asn Val Thr Val Ala Tyr Thr His Thr
65                  70                  75                  80

Gly Lys Gly Asp Lys Val Val Ile Lys Tyr Ala Phe Pro Lys Pro Ser
                85                  90                  95

Asp Tyr Glu Asn Arg Phe Tyr Val Ala Gly Gly Gly Gly Phe Ser Leu
                100                 105                 110

Ser Ser Asp Ala Thr Gly Gly Leu Ala Tyr Gly Ala Val Gly Gly Ala
            115                 120                 125

Thr Asp Ala Gly Tyr Asp Ala Phe Asp Asn Ser Tyr Asp Glu Val Val
```

-continued

```
            130                         135                         140
Leu  Tyr  Gly  Asn  Gly  Thr  Ile  Asn  Trp  Asp  Ala  Thr  Tyr  Met  Phe  Ala
145                      150                      155                      160

Tyr  Gln  Ala  Leu  Gly  Glu  Met  Thr  Arg  Ile  Gly  Lys  Tyr  Ile  Thr  Lys
                         165                      170                      175

Gly  Phe  Tyr  Gly  Gln  Ser  Ser  Asp  Ser  Lys  Val  Tyr  Thr  Tyr  Tyr  Glu
                180                      185                      190

Gly  Cys  Ser  Asp  Gly  Gly  Arg  Glu  Gly  Met  Ser  Gln  Val  Gln  Arg  Trp
               195                       200                 205

Gly  Glu  Glu  Tyr  Asp  Gly  Ala  Ile  Thr  Gly  Ala  Pro  Ala  Phe  Arg  Phe
     210                      215                      220

Ala  Gln  Gln  Gln  Val  His  His  Val  Phe  Ser  Ser  Glu  Val  Glu  Gln  Thr
225                      230                      235                      240

Leu  Asp  Tyr  Tyr  Pro  Pro  Pro  Cys  Glu  Leu  Lys  Lys  Ile  Val  Asn  Ala
                    245                      250                      255

Thr  Ile  Ala  Ala  Cys  Asp  Pro  Leu  Asp  Gly  Arg  Thr  Asp  Gly  Val  Val
               260                       265                      270

Ser  Arg  Thr  Asp  Leu  Cys  Lys  Leu  Asn  Phe  Asn  Leu  Thr  Ser  Ile  Ile
          275                      280                      285

Gly  Glu  Pro  Tyr  Tyr  Cys  Ala  Ala  Gly  Thr  Ser  Thr  Ser  Leu  Gly  Phe
     290                      295                      300

Gly  Phe  Ser  Asn  Gly  Lys  Arg  Ser  Asn  Val  Lys  Arg  Gln  Ala  Glu  Gly
305                      310                      315                      320

Ser  Thr  Thr  Ser  Tyr  Gln  Pro  Ala  Gln  Asn  Gly  Thr  Val  Thr  Ala  Arg
                    325                      330                      335

Gly  Val  Ala  Val  Ala  Gln  Ala  Ile  Tyr  Asp  Gly  Leu  His  Asn  Ser  Lys
                    340                      345                      350

Gly  Glu  Arg  Ala  Tyr  Leu  Ser  Trp  Gln  Ile  Ala  Ser  Glu  Leu  Ser  Asp
          355                      360                      365

Ala  Glu  Thr  Glu  Tyr  Asn  Ser  Asp  Thr  Gly  Lys  Trp  Glu  Leu  Asn  Ile
     370                      375                      380

Pro  Ser  Thr  Gly  Gly  Glu  Tyr  Val  Thr  Lys  Phe  Ile  Gln  Leu  Leu  Asn
385                      390                      395                      400

Leu  Asp  Asn  Leu  Ser  Asp  Leu  Asn  Asn  Val  Thr  Tyr  Asp  Thr  Leu  Val
                    405                      410                      415

Asp  Trp  Met  Asn  Thr  Gly  Met  Val  Arg  Tyr  Met  Asp  Ser  Leu  Gln  Thr
               420                      425                      430

Thr  Leu  Pro  Asp  Leu  Thr  Pro  Phe  Gln  Ser  Ser  Gly  Gly  Lys  Leu  Leu
          435                      440                      445

His  Tyr  His  Gly  Glu  Ser  Asp  Pro  Ser  Ile  Pro  Ala  Ala  Ser  Ser  Val
450                      455                      460

His  Tyr  Trp  Gln  Ala  Val  Arg  Ser  Val  Met  Tyr  Gly  Asp  Lys  Thr  Glu
465                 470                      475                      480

Glu  Glu  Ala  Leu  Glu  Ala  Leu  Glu  Asp  Trp  Tyr  Gln  Phe  Tyr  Leu  Ile
               485                      490                      495

Pro  Gly  Ala  Ala  His  Cys  Gly  Thr  Asn  Ser  Leu  Gln  Pro  Gly  Pro  Tyr
               500                      505                 510

Pro  Glu  Asn  Asn  Met  Glu  Ile  Met  Ile  Asp  Trp  Val  Glu  Asn  Gly  Asn
          515                      520                      525

Lys  Pro  Ser  Arg  Leu  Asn  Ala  Thr  Val  Ser  Ser  Gly  Thr  Tyr  Ala  Gly
     530                      535                      540

Glu  Thr  Gln  Met  Leu  Cys  Gln  Trp  Pro  Lys  Arg  Pro  Leu  Trp  Arg  Gly
545                      550                      555                      560
```

-continued

| Asn | Ser | Ser | Phe | Asp | Cys | Val | Asn | Asp | Glu | Lys | Ser | Ile | Asp | Ser | Trp |
|-----|-----|-----|-----|-----|-----|-----|-----|-----|-----|-----|-----|-----|-----|-----|-----|
|     |     |     |     | 565 |     |     |     |     | 570 |     |     |     |     | 575 |     |

| Thr | Tyr | Glu | Phe | Pro | Ala | Phe | Lys | Val | Pro | Val | Tyr |
|-----|-----|-----|-----|-----|-----|-----|-----|-----|-----|-----|-----|
|     |     |     |     | 580 |     |     |     | 585 |     |     |     |

( 2 ) INFORMATION FOR SEQ ID NO:5:

( i ) SEQUENCE CHARACTERISTICS:
        ( A ) LENGTH: 1767 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:5:

```
ATGCGCCAAC ACTCGCGCAT GGCCGTTGCT GCTTTGGCAG CAGGAGCGAA CGCAGCTTCT    60
TTTACCGATG TGTGCACCGT GTCTAACGTG AAGGCTGCAT TGCCTGCCAA CGGAACTCTG   120
CTCGGAATCA GCATGCTTCC GTCCGCCGTC ACGGCCAACC CTCTCTACAA CCAGTCGGCT   180
GGCATGGGTA GCACCACTAC CTATGACTAC TGCAATGTGA CTGTCGCCTA CACGCATACC   240
GGCAAGGGTG ATAAAGTGGT CATCAAGTAC GCATTCCCCA AGCCCTCCGA CTACGAGAAC   300
CGTTTCTACG TTGCTGGTGG TGGTGGCTTT TCCCTCTCTA GCGATGCTAC CGGAGGTCTC   360
GCCTATGGCG CTGTGGGAGG TGCCACCGAT GCTGGATACG ACGCATTCGA TAACAGCTAC   420
GACGAGGTAG TCCTCTACGG AAACGGAACC ATTAACTGGG ACGCCACATA CATGTTCGCA   480
TACCAGGCAC TGGGAGAGAT GACCCGGATC GGAAAGTACA TCACCAAGGG CTTTTATGGC   540
CAGTCCAGCG ACAGCAAGGT CTACACCTAC TACGAGGGTT GCTCCGATGG AGGACGTGAG   600
GGTATGAGTC AAGTCCAGCG CTGGGGTGAG GAGTATGACG GTGCGATTAC TGGTGCCCCG   660
GCTTTCCGTT TCGCTCAGCA ACAGGTTCAC CATGTGTTCT CGTCCGAAGT GGAGCAAACT   720
CTGGACTACT ACCCGCCTCC ATGTGAGTTG AAGAAGATCG TGAACGCCAC CATTGCTGCT   780
TGCGACCCGC TTGATGGAAG AACCGACGGT GTTGTGTCCC GGACGGATCT TTGCAAGCTT   840
AACTTCAATT TGACCTCTAT CATCGGTGAG CCTTACTACT GTGCTGCGGG AACTAGCACT   900
TCGCTTGGTT TCGGCTTCAG CAATGGCAAG CGCAGCAATG TCAAGCGTCA GGCCGAGGGC   960
AGCACCACCA GCTACCAGCC CGCCCAGAAC GGCACGGTCA CCGCACGTGG TGTAGCTGTC  1020
GCCCAGGCCA TCTACGATGG TCTCCACAAC AGCAAGGGCG AGCGCGCGTA CCTCTCCTGG  1080
CAGATTGCCT CTGAGCTGAG CGATGCTGAG ACCGAGTACA ACTCTGACAC TGGCAAGTGG  1140
GAGCTCAACA TCCCGTCGAC CGGTGGTGAG TACGTCACCA AGTTCATTCA GCTCCTGAAC  1200
CTCGACAACC TTTCGGATCT GAACAACGTG ACCTACGACA CCCTGGTCGA CTGGATGAAC  1260
ACTGGTATGG TGCGCTACAT GGACAGCCTT CAGACCACCC TTCCCGATCT GACTCCCTTC  1320
CAATCGTCCG GCGGAAAGCT GCTGCACTAC CACGGTGAAT CTGACCCCAG TATCCCCGCT  1380
GCCTCCTCGG TCCACTACTG GCAGGCGGTT CGTTCCGTCA TGTACGGCGA CAAGACGGAA  1440
GAGGAGGCCC TGGAGGCTCT CGAGGACTGG TACCAGTTCT ACCTAATCCC CGGTGCCGCC  1500
CACTGCGGAA CCAACTCTCT CCAGCCCGGA CCTTACCCTG AGAACAACAT GGAGATTATG  1560
ATCGACTGGG TCGAGAACGG CAACAAGCCG TCCCGTCTCA ATGCCACTGT TTCTTCGGGT  1620
ACCTACGCCG GCGAGACCCA GATGCTTTGC CAGTGGCCCA AGCGTCCTCT CTGGCGCGGC  1680
AACTCCAGCT TCGACTGTGT CAACGACGAG AAGTCGATTG ACAGCTGGAC CTACGAGTTC  1740
CCAGCCTTCA AGGTCCCTGT ATACTAG                                      1767
```

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC"

( i x ) FEATURE:
        ( A ) NAME/KEY: misc_difference
        ( B ) LOCATION: replace(3..4, "")
        ( D ) OTHER INFORMATION: /standard_name= "INOSINE"

( i x ) FEATURE:
        ( A ) NAME/KEY: misc_difference
        ( B ) LOCATION: replace(6..7, "")
        ( D ) OTHER INFORMATION: /standard_name= "INOSINE"

( i x ) FEATURE:
        ( A ) NAME/KEY: misc_difference
        ( B ) LOCATION: replace(9..10, "")
        ( D ) OTHER INFORMATION: /standard_name= "INOSINE"

( i x ) FEATURE:
        ( A ) NAME/KEY: misc_difference
        ( B ) LOCATION: replace(15..16, "")
        ( D ) OTHER INFORMATION: /standard_name= "INOSINE"

( i x ) FEATURE:
        ( A ) NAME/KEY: misc_difference
        ( B ) LOCATION: replace(21..22, "")
        ( D ) OTHER INFORMATION: /standard_name= "INOSINE"

( x i ) SEQUENCE DESCRIPTION: SEQ ID NO:6:

```
GGNARNGCNG  CCTTNACGTT  NGA                                              23
```

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC"

( i x ) FEATURE:
        ( A ) NAME/KEY: misc_difference
        ( B ) LOCATION: replace(3..4, "")
        ( D ) OTHER INFORMATION: /standard_name= "INOSINE"

( i x ) FEATURE:
        ( A ) NAME/KEY: misc_difference
        ( B ) LOCATION: replace(9..10, "")
        ( D ) OTHER INFORMATION: /standard_name= "INOSINE"

( i x ) FEATURE:
        ( A ) NAME/KEY: misc_difference
        ( B ) LOCATION: replace(15..16, "")
        ( D ) OTHER INFORMATION: /standard_name= "INOSINE"

( x i ) SEQUENCE DESCRIPTION: SEQ ID NO:7:

```
ACNGTRCANA  CRTCNGTGAA                                                   20
```

( 2 ) INFORMATION FOR SEQ ID NO:8:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
  ( A ) DESCRIPTION: /desc = "SYNTHETIC"

( i x ) FEATURE:
  ( A ) NAME/KEY: misc_difference
  ( B ) LOCATION: replace(3..4, "")
  ( D ) OTHER INFORMATION: /standard_name= "INOSINE"

( i x ) FEATURE:
  ( A ) NAME/KEY: misc_difference
  ( B ) LOCATION: replace(6..7, "")
  ( D ) OTHER INFORMATION: /standard_name= "INOSINE"

( i x ) FEATURE:
  ( A ) NAME/KEY: misc_difference
  ( B ) LOCATION: replace(21..22, "")
  ( D ) OTHER INFORMATION: /standard_name= "INOSINE"

( x i ) SEQUENCE DESCRIPTION: SEQ ID NO:8:

CGNACNGCCT GCCARTARTG NAC    23

( 2 ) INFORMATION FOR SEQ ID NO:9:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:9:

CTGCCATTCT TTTGGTTCGA    20

( 2 ) INFORMATION FOR SEQ ID NO:10:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:10:

GTTTCCCAG TCACGACTTT TTTTTTTTT TTTTTT    37

DNA FRAGMENT CONTAINING A TANNASE GENE, A RECOMBINANT PLASMID, A PROCESS FOR PRODUCING TANNASE, AND A PROMOTER

FIELD OF THE INVENTION

The present invention relates to a DNA fragment containing a tannase gene, a recombinant plasmid comprising said DNA fragment linked to a plasmid vector, a process for producing tannase, and a promoter.

BACKGROUND OF THE INVENTION

Tannase is an extremely useful enzyme for use as an inhibitor of cream down in tea or a clarifier in the production of beer.

Conventionally, tannase has been produced by culturing a microorganism belonging to *Aspergillus oryzae* capable of producing tannase in special medium containing tannic acid etc. (Japanese Patent Publication No. 8584/81).

However, the conventional process of producing tannase was not satisfactory with respect to tannase yield, etc.

Hence, the problem of the present invention is to produce tannase by genetic engineering means to increase the yield.

Under such circumstances, the present inventors found that tannase can be efficiently obtained from a culture of bacteria belonging to the genus Aspergillus carrying a recombinant plasmid prepared by inserting into a plasmid vector a DNA fragment containing a gene coding for tannase.

SUMMARY OF THE INVENTION

That is, an aspect of the present invention relates to a DNA fragment of 3,563 base pairs containing a gene coding for tannase and derived from bacteria belonging to the genus Aspergillus, with the following restriction enzyme map:

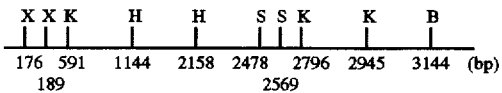

B: Bam HI, H: Hind III, K: Kpn. I, S: Sal I, X: Xba I

Another aspect of the present invention relates to a DNA fragment containing a tannase gene coding for an amino acid sequence substantially represented by Sequence No. (SEQ ID NO:4).

The "amino acid sequence substantially represented by (SEQ ID NO:4)" may have been modified in some amino acids by deletion, replacement, addition, etc., insofar as the tannase activity is maintained.

As a matter of course, the tannase gene may, besides the nucleotide sequence coding for the amino acid sequence shown in (SEQ ID NO:4), include a degenerated isomer coding for the same polypeptide with a difference in only degeneracy.

A further aspect of the present invention relates to a recombinant plasmid comprising said DNA fragment containing the tannase gene inserted into a plasmid vector.

A still other aspect of the present invention relates to a process for producing tannase which comprises culturing a microorganism belonging to the genus Aspergillus capable of producing tannase in medium with said recombinant plasmid, and recovering tannase from the culture.

A still further aspect of the present invention relates to the promoter (SEQ ID NO: 1).

Figure 1:
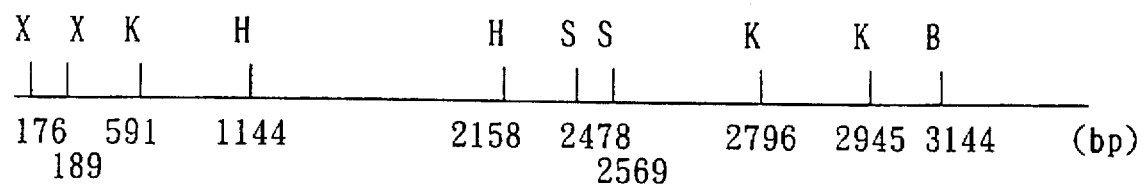
FIG. 1 shows a restriction enzyme map of the DNA fragment containing the gene coding for tannase.

DETAILED DESCRIPTION OF THE INVENTION (I) Preparation of a probe for use in cloning of the tannase gene In the first step, a probe is prepared for cloning of the tannase gene as will be described below.

As the tannase-producing bacteria, there may be employed any strain belonging to the genus Aspergillus including *Aspergillus oryzae* IAM 2636, *Aspergillus oryzae* IAM 2704, etc.

To culture the tannase-producing bacteria, the medium contains e.g. carbon sources, nitrogen sources, inorganic salts, etc., admixed therein.

Examples of carbon sources are glucose, fructose, galactose, mannose, xylose, glycerin, saccharose, dextrin, mannitol, mannose, molasses, etc.

Examples of nitrogen sources are polypeptone, $NaNO_3$, $NaNO_2$, $(NH_4)_2HPO_4$, $NH_4H_2PO_4$, etc.

Examples of inorganic salts are $KH_2PO_4$, $K_2HPO_4$, $NaNO_3$, $MgSO_4$, $CaCl_2$, $FeSO_4$, $ZnSO_4$, KCl, etc.

The bacteria are cultured e.g. for about 40 to 60 hours at a temperature of 25° to 35° C., preferably 28° to 32° C., in shake culture, spinner culture under aeration, etc. Under tannase-inducing conditions, for example, 0.1 to 6% tannic acid is added to the medium.

The medium is adjusted initially within the range of pH 5.0–6.5, and during incubation, no pH adjustment is required.

A purified tannase preparation can be obtained from the culture in the following manner: The culture is filtered to remove bacteria, and the filtrate is precipitated with solvent such as acetone, alcohol, etc., or by salting out with ammonium sulfate, etc. The crude enzyme powder thus obtained is further subjected to a suitable combination of the absorption-elution method on ion exchange resin such as diethylaminoethyl (DEAE) cellulose, DEAE Sephadex, etc., gel filtration on Sephadex G-100, etc., the absorption-elution method on other carriers, electrophoresis, etc.

The tannase preparation thus purified can be used to determine a partial amino acid sequence of tannase according to the method described by P. Edman (Acta. Chem. Scand., 4, 283 (1950)) or M. W. Hunkapiller and L. E. Hood (Science, 219, 650 (1983)) after hydrolysis with cyanogen bromide according to the method described by E. Gross (Methods in Enzymology, 11, 238). On the basis of the partial amino acid sequence thus determined, a probe of about 20 bp can be prepared in a DNA synthesizer (manufactured by Applied Biosystems) according to the manufacturer's instructions.

(II) Cloning of the tannase gene

The donor of the gene coding for tannase may be any microorganism belonging to the genus Aspergillus, including *Aspergillus oryzae* IAM 2636, *Aspergillus oryzae* IAM 2704, etc.

The tannase gene on the genomic DNA derived from a strain of the genus Aspergillus can be cloned according to the modified method described in Molecular Cloning A LABORATORY MANUAL, 2nd edition, Vol. 1, p. 1.85–1.104 and p. 7.19–7.22 as is described below.

First, the above donor bacteria are cultured under the above conditions, and then genomic DNA is obtained according to the method described in Example 1, item (2) and digested with several restriction enzymes. The mixture of DNA fragments may be subjected to Southern hybridization with each of the above labeled probes to identify a fragment containing the tannase gene. The fragment indicating a strong signal with each labeled probe is cut off and purified.

Then, a recombinant plasmid is prepared by inserting the above isolated DNA fragment into a plasmid vector with which bacteria such as *E. coli* JM 109 (produced by Takara Shuzo Co., Ltd.) are then transformed to give transformants. Transformation can be effected by the calcium chloride method.

The plasmid vector that can be used include plasmids such as pUC 18, pUC 19, pUC 118, pUC 119 and pBR 322 DNA.

Colony hybridization with the above probe can identify a recombinant plasmid containing the target gene. Cells of the positive colonies are removed and cultured to produce a large amount of the desired recombinant DNA fragment.

From the transformant indicating a strong signal in colony hybridization, the recombinant plasmid is collected. The vector DNA is removed from it whereby a DNA fragment containing the tannase gene is obtained. This fragment is cleaved with restriction enzymes and analyzed by agarose gel electrophoresis etc., so that a restriction enzyme map of the tannase gene-containing DNA fragment is obtained.

The nucleotide sequence of said DNA fragment can be determined using Taq Dye Primer Cycle Sequencing Kit or Taq Dye Deoxy TM Terminator Cycle Sequencing Kit (produced by Applied Biosystems) according to the manufacturer's instructions.

The above bacterial donor is cultured under tannase-inducing conditions and separated from the culture, and mRNA is obtained from it according to the method described in Example 1, item (7). The target DNA fragment coding for tannase is prepared as the reverse transcription product of the tannase mRNA. This DNA fragment is then inserted into a plasmid vector to give a recombinant plasmid. The recombinant plasmid can be used to determine the nucleotide sequence of the DNA fragment obtained in the reverse transcription of the tannase mRNA.

The sequence of an intron in the tannase gene and the amino acid sequence encoded by the tannase gene can be determined by comparing the nucleotide sequence of the DNA fragment obtained with the tannase mRNA, with the nucleotide sequence of the tannase gene obtained with the genomic DNA.

(III) Transformant and tannase expression

The host used for tannase expression in the invention may be any microorganism belonging to the genus Aspergillus, and preferably used is *Aspergillus oryzae* TL-1 (FERM BP-4720), that is a NiaD$^-$ deficient variant (nitrate reductase-deficient strain) derived from *Aspergillus oryzae* TL strain.

Transformation of the host with the above recombinant plasmid can be effected according to the method described in Curr. Genet., 16, 53–56 (1989).

The resulting transformants are screened for bacteria capable of high-level production of tannase, whereby bacteria belonging to the genus Aspergillus capable of producing tannase with the recombinant plasmid can be obtained.

The bacteria belonging to the genus Aspergillus capable of producing tannase with the recombinant plasmid are cultured in the above medium containing 0.1 to 6% tannic acid under the conditions described above, and the culture is used for the preparation of purified tannase.

The physicochemical properties of the tannase thus obtained are in complete agreement with those described e.g. by S. Iibuchi, Y. Minoda and K. Yamada, Agr. Biol. Chem., 32, 803 (1968).

According to the present invention, there are provided a DNA fragment containing a gene coding for tannase and a recombinant plasmid having said DNA fragment inserted into a plasmid vector. Tannase can be sufficiently produced by culturing the bacteria of the genus Aspergillus capable of producing tannase with said recombinant plasmid.

The present invention is described in more detail with reference to the following example, which however is not intended to limit the scope of the present invention.

EXAMPLE

[Reference Example 1] Tannase preparation for determining a partial amino acid sequence thereof 20 liters of a modified medium containing 2% tannic acid, 1% glucose, 1.4% monobasic antimony phosphate, 0.2% $KH_2PO_4$, 0.05% $MgSO_4 \cdot 7H_2O$, pH 5.5 (adjusted with 5N NaOH) (in the medium, glucose (%)/tannic acid (%)=0.5, C/N=8.6) was introduced without sterilization into a fermentation chamber (volume: 30 liters), followed by inoculation with spores of *Aspergillus oryzae* TH strain (IAM 2636) and the bacteria were incubated at 30° C. for 48 hours with stirring at 400 r.p.m. under aeration at 20 liters/min. The tannase activity of the culture filtrate was 12 U/ml. After 48 hours of incubation, the culture was filtered with Celite as filter aid, and the filtrate, 15 liters, was concentrated into 3 liters under reduced pressure at a temperature of 25° C., and the enzyme was precipitated with a 3-fold excess volume of cold acetone (0° C.), then centrifuged and dried under reduced pressure to give 19.0 g powder of crude tannase. The recovery of the tannase from the culture filtrate was 72% and the specific activity of the enzyme powder was 6,800 U/g.

Then, 2 g of the crude enzyme powder was dissolved in 20 ml of 0.01M sodium acetate-acetic acid buffer, pH 5.5, centrifuged for removal of insolubles and applied to a DEAE cellulose column equilibrated with the same buffer. The absorbed enzyme was eluted with an increasing concentration of sodium chloride (gradient elution from 0 to 1M NaCl). The tannase fractions (220 ml) were combined and desalted by dialysis against the same buffer and then lyophilized. The resulting preparation was dissolved in 3 ml of 0.01M acetic acid-ammonium buffer, pH 5.5, and subjected to gel filtration through a Sephadex G-100 column equilibrated with the same buffer. The eluted tannase fraction (30 ml) was lyophilized to give 80.6 mg purified enzyme preparation (specific activity: 77,000 U/g, recovery: 45%).

Example 1

Cloning of genomic tannase DNA derived from *Aspergillus oryzae* TH strain (1) Acquisition of the microorganism $1.2 \times 10^5$ spores of *Aspergillus oryzae* TH strain (IAM 2636) were inoculated into 200 ml growth medium [2% (W/V) dextrin, 1% (W/V) polypeptone, 0.5% (W/V) $KH_2PO_4$, 0.1% (W/V) $NaNO_3$, 0.05% (W/V) $MgSO_4$, pH 5.7] and cultured for 40 hours with stirring at 120 r.p.m. at a temperature of 30° C. The culture was filtered to give 10 g bacteria.

(2) Preparation of genomic DNA

The bacteria were suspended in 20 ml buffer for protoplast preparation (0.6M KCl, 0.093M $NaH_2PO_4$, 0.007M $Na_2HPO_4$, pH 5.5) containing 0.1 g Novozyme 234 (produced by Novo Nordisk) and stirred at 75 r.p.m. for 2 hours at a temperature of 30° C. The resulting protoplast solution was filtered through sterilized Kimwipe (produced by Juzyo Kimberly) to remove the bacteria residue, and the filtrate was centrifuged at 1,000 r.p.m. for 10 min. The precipitate was suspended in 20 ml buffer for protoplast preparation and centrifuged at 1,000 r.p.m. for 10 min. The resulting precipitate was suspended in 5 ml buffer for protoplast disruption [50 mM Tris-HCl, 0.15M NaCl, 100 mM EDTA, 2% (W/V) sodium lauryl sulfate, pH 7.5] and allowed to stand for 1 hour at 37° C., followed by addition of 50 μl protease solution [1% (W/V) Proteinase K (produced by Wako Junyaku)] and the sample was allowed to stand for 18 hours at a temperature of 37° C.

This solution was then suspended in 5 ml of phenol saturated with TE buffer (10 mM Tris-HCl, 1 mM EDTA, pH 7.5) and centrifuged at 12,000 r.p.m. for 10 min. The upper aqueous layer was removed and suspended in 5 ml mixed solvent consisting of 24 parts of chloroform and 1 part of isoamyl alcohol by volume and centrifuged at 12,000 r.p.m. for 10 min. The upper aqueous layer was removed and suspended in 5 ml diethyl ether and centrifuged at 12,000 r.p.m. for 10 min. The lower aqueous layer was saved and allowed to stand at 68° C. for 10 min.

To this DNA solution was added 5 ml polyethylene glycol solution [20% (W/V) polyethylene glycol 3000, 2M NaCl], and the solution was allowed to stand for 1 hour on ice and then centrifuged at 2,000 r.p.m. for 10 min. The formed precipitate was washed with 70% (V/V) cold ethanol, evaporated to dryness and suspended in 1 ml TE buffer, followed by addition of 10 μl of 0.1% (W/V) RNase previously heated at 100° C. for 10 min. The sample solution was then allowed to stand at 37° C. for 1 hour, and 1 ml of phenol saturated with TE buffer was added thereto and suspended, and the suspension was centrifuged at 12,000 r.p.m. for 10 min. The upper aqueous layer was removed and suspended in 1 ml mixed solvent consisting of 24 parts of chloroform and 1 part of isoamyl alcohol by volume and centrifuged at 12,000 r.p.m. for 10 min. The upper aqueous layer was removed and suspended in 1 ml diethyl ether and centrifuged at 12,000 r.p.m. for 10 min. The lower aqueous layer was saved and allowed to stand at 68° C. for 10 min. To the solution were added a 1/10 volume of 3M sodium acetate, pH 5.2, and a 2-fold excess volume of cold ethanol, and the solution was allowed to stand at −80° C. for 30 min. and centrifuged at 12,000 r.p.m. for 10 min. The precipitate was washed with 70% (V/V) cold ethanol, evaporated to dryness, and suspended in 1 ml TE buffer to give a genomic DNA solution.

(3) Determination of a partial amino acid sequence of tannase 1 mg tannase obtained in Reference Example 1 and 30 mg CNBr were added to 2.1 ml formic acid and the total volume was adjusted to 3 ml with distilled water. The solution was introduced into a round-bottom flask which was then sealed with Parafilm and stirred at 40 r.p.m. for 24 hours at a temperature of 25° C.

This sample was evaporated to dryness, then suspended in 200 μl of 0.2N acetic acid and centrifuged at 12,000 r.p.m. for 10 min. The supernatant was subjected to high performance liquid chromatography in a gradient for 40 min. of from 0% acetonitrile and 0.1% TFA to 80% acetonitrile and 0.1% TFA. The fraction of each peak was collected, evaporated to dryness and dissolved in 20 μl sterilized water. A partial amino acid sequence of tannase (Sequence No. 2) was determined in a protein sequencer (manufactured by Applied Biosystems). Separately, 20 μg tannase was analyzed in the same manner for N-terminal amino acid sequence in the protein sequencer (Sequence No. 3).

(4) Preparation of probes

On the basis of the determined amino acid sequences, the following probes 1 to 3 were synthesized in a DNA synthesizer (manufactured by Applied Biosystems) and used in subsequent colony hybridization.

Probe 1 (SEQ ID NO:6): 5' GGI A(AG)I GCI GCC TTI ACG TTI GA 3'

Probe 2 (SEQ ID NO:7): 5' ACI GT(AG) CAI AC(AG) TCI GTG AA 3'

Probe 3 (SEQ ID NO:8): 5' CGI ACI GCC TGC CA(AG) TA(AG) TGI AC 3'

1 pmol of each probe DNA was added to 19 μl kination buffer (50 mM Tris-HCl, 10 mM $MgCl_2$, 10 mM 2-mercpatoethanol, 100 μM [$\gamma$-$^{32}$P]ATP, pH 7.6), followed by addition of 1 μl of T4 polynucleotide kinase (10 U/μl). Each probe solution was allowed to stand at 37° C. for 30 min. and then purified through a Nensorb 20 cartridge (produced by Daiichi Kagaku Yakuhin) for nucleic acid purification, to give 100 μl of each labeled probe solution.

(5) Southern hybridization

50 μl DNA solution of 20 μg genomic DNA obtained above from Aspergillus oryzae TH strain was treated with restriction enzyme Eco RI, Bam HI, Hind III or Pst I, and 10 μl of each DNA solution was subjected to agarose gel electrophoresis. For blotting, a glass plate was placed on a glass vessel in 0.4M NaOH contained in a tray, and a filter paper was placed so as to cover the glass plate. The above gel was placed on the filter paper, and the part other than the gel was covered with a wrapping film. The gel was covered with a nylon filter membrane (produced by Amersham) of the same size as the gel, and on the nylon filter membrane, 3 sheets of filter papers of the same size as the gel, a paper towel, a glass plate and 0.5 kg weight were placed in this order. The DNA fragments were transferred to the nylon membrane by blotting for 2 hours. Then, the membrane was washed with 5× SSC buffer (0.75M NaCl, 75 mM sodium citrate) and subjected to prehybridization under shaking at 42° C. for 1 hour in a hybridization solution [0.75M NaCl, 75 mM sodium citrate, 0.1% (W/V) BSA, 0.1% (W/V) Ficoll, 0.1% (W/V) polyvinyl pyrrolidone, 0.5% (W/V) SDS, 0.5 mg sssDNA (which was prepared by ultrasonication, heating for 5 min. in boiling water and rapidly cooling)]. Then, the membrane was subjected to hybridization at 42° C. for 16 hours in a hybridization solution containing 20 μl of thermally denatured labeled probe 1. After hybridization, the membrane was immersed in washing solution 1 (0.75M NaCl, 75 mM sodium citrate, 1% SDS) and shaken at 42° C. for 10 min. The membrane was removed and immersed again in washing solution 1 and shaken at 42° C. for 10 min. Then, the membrane was washed with washing solution 2 (0.15M NaCl, 15 mM sodium citrate) and shaken at 37° C. for 10 min. The membrane was removed and immersed again in washing solution 2 and shaken at 37° C. for 10 min. The membrane was taken out and excess water was wiped off on a filter paper. It was then wrapped in a wrapping film and subjected to autoradiography at −70° C. for 16 hours. Additional autoradiography was conducted with the labeled probes 2 and 3 respectively in the same manner. A DNA solution of 4 μg genomic DNA treated with restriction enzyme Eco RI was subjected to agarose gel electrophoresis and stained with ethidium bromide, and a DNA fragment of 3.3 to 3.6 kbp indicating a strong signal with each of the labeled probes 1, 2 and 3 was cut off and purified using Prep A Gene DNA Purification Matrix Kit (produced by Bio-Rad).

(6) Colony hybridization 0.1 μg plasmid pUC19 was treated restriction enzyme Eco RI and then dephosphorylated, and the above purified DNA fragment was ligated with this plasmid pUC19 with a DNA ligation kit (produced by Takara Shuzo Co., Ltd.).

The recombinant plasmid DNA thus obtained was transformed into calcium chloride-treated E. coli JM 109 (produced by Takara Shuzo Co., Ltd.) according to the D. M. Morrison method [Methods in Enzymology, 68, 326–331 (1979)].

A nylon filter membrane (produced by Amersham) was placed for about 1 min. on a medium plate with the growing transformant, then removed and placed on a sterilized filter paper with the colony side up. Then, the membrane was removed and placed for 7 min. with the colony side up on a filter paper immersed with a denaturation solution (1.5M NaCl, 0.5M NaOH). The membrane was removed and placed for 3 min. with the colony side up on a filter paper impregnated with a neutralization solution (1.5M NaCl, 0.5M Tris-HCl, mM EDTA, pH 7.2) and then placed for another 3 min. on another filter paper with a neutralization solution. The membrane was washed for 1 min. with a 2× SSC buffer (0.3M NaCl, 0.03M sodium citrate) and then air-dried with the colony side up on a dried filter paper. The dried membrane was removed, placed for 20 min. on a filter paper impregnated with 0.4M NaOH and shaken for 1 min. in a 5× SSC buffer.

Subsequently, the membrane was subjected to prehybridization for 1 hour at 42° C. under shaking in the hybridization solution. The membrane was further subjected to hybridization at 42° C. for 16 hours under shaking in the hybridization solution containing 20 µl of thermally denatured labeled prove 1. After hybridization, the membrane was immersed in washing solution 1 and shaken at 42° C. for 10 min. The membrane was removed, immersed again in washing solution 1 and shaken at 42° C. for 10 min. Then, the membrane was immersed in washing solution 2 and shaken at 37° C. for 10 min. The membrane was removed and immersed again in washing solution 2 and shaken at 37° C. for 10 min. The washed membrane was taken out, and after excess water was wiped off on a filter paper, it was wrapped in a wrapping film and subjected to autoradiography at −70° C. for 16 hours.

(7) Determination of the nucleotide sequence of the tannase gene

The transformant indicating a strong signal in autoradiography was inoculated into 250 ml TY medium [1% (W/V) Bacto-trypton, 0.5% (W/V) Bacto-yeast extract, 0.5% (W/V) NaCl, pH 7.2] containing 12.5 mg ampicillin and then cultured at 37° C. for 20 hours under shaking.

The culture was centrifuged at 5,000 r.p.m. for 10 min. and centrifuged to give wet bacteria which were then suspended in 5 ml STET buffer [10 mM Tris-HCl, 50 mM EDTA, 8% (W/V) sucrose, 0.5% (W/V) Triton X-100, pH 8.0] and lysed with 25 mg lysozyme for 5 min. at room temperature.

After addition of 10 ml of 0.2N NaOH containing 1% (W/V) SDS, the lysed solution was allowed to stand at 0° C. for 10 min. for denaturation of the DNA. Then, 7.5 ml of 5M sodium acetate-acetic acid buffer, pH 4.8, was added thereto and the DNA solution was allowed to stand at 0° C. for 20 min., whereby only the plasmid DNA was regenerated. The solution was centrifuged at 9,000 r.p.m. for 20 min. to give an extract which was then subjected to extraction with chloroform and precipitated with ethanol.

The precipitate was dried under reduced pressure and dissolved in 6 ml TE buffer, followed by addition of 6 g cesium chloride and 0.3 ml of 10 mg/ml ethidium bromide. This sample was separated by equilibrium density-gradient centrifugation at 50,000 r.p.m. for 20 hours in a ultracentrifuge. From the recombinant plasmid thus isolated, the ethidium bromide was removed by extraction with n-butanol, and the plasmid solution was dialyzed against a TE buffer to give 100 µg purified recombinant plasmid pT1.

A DNA fragment of about 3.5 kbp estimated to code for tannase in plasmid pT1 excluding the sequence of plasmid pUC19 was analyzed by rising the restriction enzyme sites. FIG. 1 shows the restriction enzyme map.

The DNA fragment was further cleaved with restriction enzymes and the resulting DNA fragments were subcloned into a multicloning site of plasmid pUC118 or pUC119 with which E. coli JM 109 (produced by Takara Shuzo Co., Ltd.) was then transformed to give transformants.

A single-stranded DNA was prepared from each transformant according to the Messing method [Methods in Enzymology, 101, 20–78 (1983)] after infection with helper phage M13K07 (produced by Takara Shuzo Co., Ltd.).

Sequencing of the single-stranded DNA was conducted according to the Messing method with Taq Dye Primer Cycle Sequencing Kit (produced by Applied Biosystems). Gel electrophoresis for analysis of nucleotide sequence was conducted in DNA sequencer 370A (manufactured by Applied Biosystems) on 6% (W/V) polyacrylamide gel (produced by National Diagnostics) containing 50% (W/V) urea.

The analysis of the nucleotide sequence indicated the presence of 1 open reading frame assumed to code for tannase, containing the nucleotide sequence estimated from the N-terminal amino acid sequence and the partial amino acid sequence determined in item (3) above, as well as regions assumed respectively to be a promoter and terminator.

The nucleotide sequence of the promoter region is shown in (SEQ ID NO:1).

Then, the intron sequence in the tannase gene and the amino acid sequence of tannase encoded by the tannase gene were determined as described below by comparing the nucleotide sequence of the DNA fragment obtained by the RT-PCR method from the mRNA, with the nucleotide sequence of the DNA fragment containing the tannase gene isolated from the genomic DNA, from Aspergillus oryzae TH strain (IAM 2636) cultured under tannase-inducing conditions.

First, $1.2 \times 10^5$ spores of Aspergillus oryzae TH strain (IAM 2636) were inoculated into 200 ml growth medium [2% (W/V) dextrin, 1% (W/V) polypeptone, 0.5% (W/V) $KH_2PO_4$, 0.1% (W/V) $NaNO_3$, 0.05% (W/V) $MgSO_4$, pH 5.7] and cultured for 40 hours at 30° C. with stirring at 120 r.p.m. and the culture was filtered to give 10 g bacteria.

The bacteria were inoculated into tannic acid liquid medium [2.5 tannic acid, 5.3% (W/V) glucose, 1.2% (W/V) $(NH_4)_2PO_4$, 0.2% (W/V) $KH_2PO_4$, 0.1% (W/V) $MgSO_4$, pH 6.8] and cultured for 5 hours at 30° C. under shaking and the culture was filtered to give 10 g bacteria.

The bacteria were added to 20 ml guanidine isothiocyanate solution [6M guanidine isothiocyanate, 37.5 mM sodium citrate (pH 7.0), 0.75% (W/V) sodium N-lauroyl sarcosine, 0.15M β-mercaptoethanol] and then introduced to a cup type blender (manufactured by Hitachi Seiki Seisakusho) to which 10 g glass beads of 0.5 mm diameter were introduced, and the bacteria were ground at 10,000 r.p.m. for 5 min., and after addition of 10 ml water-saturated phenol, at 10,000 r.p.m. for 10 min. The disrupted bacteria were centrifuged at 5,000 r.p.m. for 10 min. in a cooling centrifuge (manufactured by Hitachi Koki) to give 20 ml supernatant.

Then, the supernatant was layered over 1.2 ml of 5.7M cesium chloride in each of 4 ultracentrifugation tubes and centrifuged at 15° C. at 30,000 r.p.m. for 16 hours in a ultracentrifugate (manufactured by Hitachi Koki).

The resulting precipitate was washed with 70% (W/V) cold ethanol, then suspended in 4 ml of 10 mM Tris-HCl buffer, pH 7.4 containing 5 mM EDTA and 1% SDS, extracted with an equal volume of a mixed solvent of n-butanol and chloroform (4:1 (V/V)), and centrifuged at 3,000 r.p.m. for 10 min. The lower aqueous layer was removed, followed by addition of a 1/10 volume of 3M sodium acetate (pH 5.2) and a 2-fold excess volume of cold ethanol. The sample was allowed to stand −20° C. for 2 hours and centrifuged at 8,000 r.p.m. for 20 min. The precipitated RNA was then dissolved in 4 ml water, extracted with ethanol and dissolved in 1 ml water to give 12 mg RNA.

The mRNA was purified with Oligotex™ dT30 <Super> (produced by Takara Shuzo Co., Ltd.) and used for the preparation of a 2060 bp DNA fragment containing the tannase gene with RNA PCR Kit and LA PCR Kit (both produced by Takara Shuzo Co., Ltd.). 1 cycle of the RT reaction at 42° C. for 45 min., 99° C. for 5 min. and 5° C.

for 5 min. was conducted in the presence of the following Oligo(dt)$_{20}$-M4 Adaptor primer. 30 cycles of the PCR reaction at 94° C. for 0.5 min., 60° C. for 1 min. and 72° C. for 3.5 min. were conducted in the presence of the sense primer located 23 bp upstream from the origin of replication of the tannase gene and the antisense Oligo(dT)$_{20}$-M4 Adapter primer as shown below.

sense primer (SEQ ID NO:9): CTG CCA TTC TTT TGG TTC GA 3'

Oligo(dt)$_{20}$-M4 Adaptor primer (SEQ ID NO:10): 5' GTT TTC CCA GTC ACG ACT TTT TTT TTT TTT TTT TTT T 3'

Separately, 0.1 µg of plasmid pUC19 was treated with restriction enzyme Sma I and then dephosphorylated. This cleaved plasmid was ligated with the resulting DNA fragment with a DNA ligation kit (produced by Takara Shuzo Co., Ltd.), whereby a recombinant plasmid was obtained.

The recombinant plasmid was transformed into calcium chloride-treated *E. coli* JM109 (available from Takara Shuzo Co., Ltd.) according to the D. M. Morrison method [Methods in Enzymology, 68, 326–331 (1979)]. In the same manner as described above, a DNA fragment of 2060 bp was obtained from the transformant in the RT-PCR method and was then sequenced.

The result indicated that the tannase gene was an intron-free gene coding for tannase with the amino acid sequence of (SEQ ID NO:4), and that the tannase gene was composed of the nucleotide sequence of (SEQ ID NO:5).

Example 2

Transformant and tannase expression
(1) Host for use in transformation

As the host to be transformed, a NiaD$^-$ variant (nitrate reductase-deficient strain) was obtained in the following manner from *Aspergillus oryzae* TL strain, that is a strain derived by spontaneous mutation from *Aspergillus oryzae* TH strain (IAM 2636).

The *Aspergillus oryzae* TL strain was inoculated onto a malt medium plate [8% (W/V) malt extract, 2% (W/V) agar, pH 6.5] and cultured at 30° C. for 4 days. After the spores were adhered to the medium, 5 ml of 0.01% sterilized Sorgen solution was put to the plate and the spores were scratched off and filtered through 3G-2 filter (produced by Pyrex), whereby a spore suspension was obtained. 100 µl of the spore suspension was inoculated into minimum medium [1% (W/V) glucose, 0.05% (W/V) KCl, 0.05% (W/V) MgSO$_4$.7H$_2$O, 0.15% (W/V) KH$_2$PO$_4$, 0.000004% (W/V) Na$_2$B$_4$O$_7$.10H$_2$O, 0.00004% (W/V) CuSO$_4$.5H$_2$O, 0.00008% (W/V) FePO$_4$.2H$_2$O, 0.00008% (W/V) MnSO$_4$.2H$_2$O, 0.00008% (W/V) Na$_2$MoO$_4$.2H$_2$O, 0.0008% (W/V) ZnSO$_4$.7H$_2$O] and cultured at 30° C. for 4 days.

Then, the resulting transformant was inoculated into 5 kinds of minimum medium containing 2% (W/V) agar and 10 mM NaNO$_3$, 10 mM NaNO$_2$, 10 mM glutamic acid, 10 mM NH$_4$Cl or 10 mM hypoxanthine, and a transformant which could grow in these media except for the medium containing sodium nitrate was selected and designated *Aspergillus oryzae* TL-1 strain. This transformant has been deposited as FERM BP-4720 with the National Institute of Bioscience and Human-Technology, Agency of Industrial Science and Technology, Japan.

(2) Tannase expression 1.2×10$^5$ spores of *Aspergillus oryzae* TL-1 strain were inoculated into 200 ml growth medium and cultured at 30° C. for 40 hours with stirring at 120 r.p.m., and the culture was filtered to give 10 g. bacteria. The bacteria were suspended in 50 ml buffer for protoplast preparation and then filtered. The resulting bacteria were suspended in 20 ml buffer for protoplast preparation containing 0.1 g Novozyme 234 (produced by Novo Nordisk) and stirred at 75 r.p.m. at 30° C. for 2 hours. This bacteria solution was then filtered through Kimwipe (manufactured by Juzyo Kimberly).

To the resulting protoplast solution was added a 4-fold excess volume of transformation solution 1 (1.2M sorbitol, 50 mM CaCl$_2$, 10 mM Tris-HCl, pH 7.5) and the sample was centrifuged at 2,000 r.p.m. for 5 min. at room temperature. The precipitate was suspended in 20 ml transformation solution 1 and centrifuged at 2,000 r.p.m. for 5 min. at room temperature, and the precipitate was suspended in 100 µl transformation solution 1. To the resulting protoplast solution were added 10 µg plasmid pT1 and 10 µl DNA solution of 10 µg plasmid pMD4 containing NiaD gene coding for nitrate reductase, and the mixture was stirred followed by addition of 12.5 µl transformation solution 2 [50% (W/V) PEG 4000, 50mM CaCl$_2$, 10 mM Tris-HCl, pH 7.5] and it was allowed to stand for 20 min. on ice. Then, 1 ml transformation solution 2 was added to the mixture of the protoplast and DNA, and then mixed gently for a short time, and 2 ml transformation solution 1 was added thereto and mixed gently for a short time. This mixture was then added to 100 ml minimum medium (0.5% agar, 1.2M sorbitol and 10 mM NaNO$_3$) previously heated at 55° C., and they were sufficiently mixed. Each 5 ml aliquot was overlaid on a minimum medium plate containing 2% agar, 1.2M sorbitol and 10 mM NaNO$_3$ and then cultured at 30° C. for 5 days.

The transformant spores thus obtained were spot-inoculated onto a tannic acid medium plate [0.2% (W/V) (NH$_4$)$_2$HPO$_4$, 0.2% (W/V) KH$_2$PO$_4$, 0.1% (W/V) MgSO$_4$.7H$_2$O, 1% (W/V) glucose, 1% (W/V) tannic acid, 2% (W/V) agar, pH 7.5] and a malt medium plate and cultured at 30° C. for 40 hours. The transformants on the malt medium plate corresponding to the transformants forming a large hollow on the tannic acid medium plate were further cultured at 30° C. for 80 hours. The transformant spores thus obtained were scratched off with a toothpick and suspended in 0.01% sterilized Sorgen solution. The suspension was diluted so as to form 5 to 10 colonies per plate and inoculated onto a malt medium plate. Then, each transformant was obtained in single colony isolation, and transformant *Aspergillus oryzae* TL+8 (pT1) forming a large hollow in the tannic acid medium was selected by repeating the same operation 5 times.

The transformant *Aspergillus oryzae* TL+8 (pT1) has been deposited as FERM BP-4719 with the National Institute of Bioscience and Human-Technology, Agency of Industrial Science and Technology, Japan.

(3) Analysis of the transformant

10 µl DNA solution of 2 µg plasmid pT1 was treated with restriction enzyme Hind III, then subjected to agarose gel electrophoresis and stained with ethidium bromide. A fragment of about 1 kbp located on the open reading frame was cut off and purified with Prep A Gene DNA Purification Matrix Kit (produced by Bio Rad), followed by labeling with DIG DNA Labeling Kit (produced by Boehringer Mannheim).

Then, genomic DNAs were obtained respectively from the transformant *Aspergillus oryzae* TL+8 (pT1) and the parent strain *Aspergillus oryzae* TL-1 in the same manner as in Example 1 (2), and 10 µl DNA solution of 4 µg of each genomic DNA was treated with restriction enzyme Bam HI and subjected to agarose gel electrophoresis. For blotting, a glass plate was placed on a glass vessel in 0.4M NaOH contained in a tray, and a filter paper was placed so as to cover the glass plate. The above gel was placed on the filter paper, and the part other than the gel was covered with a wrapping film. The gel was covered with a nylon filter membrane (produced by Amersham) of the same size as the gel, and on the nylon filter membrane, 3 sheets of filter papers of the same size as the gel, a paper towel, a glass plate and 0.5 kg weight were placed in this order. The DNA fragments were transferred to the nylon membrane by blotting for 2 hours. Then, the membrane was washed with 5× SSC buffer and subjected to prehybridization under shaking at 42° C. for 1 hour in the hybridization solution. Then, the membrane was subjected to hybridization at 42° C. for 16 hours in 10 ml hybridization solution containing 100 ng of the thermally denatured labeled probe. After hybridization, the membrane was immersed in washing solution 3 [0.3M NaCl, 30 mM sodium citrate, 1% (W/V) SDS] and shaken for 5 min. at room temperature. The membrane was removed and immersed again in washing solution 3 and shaken for 5 min. at room temperature. Then, the membrane was washed with washing solution 4 [15 mM NaCl, 1.5 mM sodium citrate, 0.1% (W/V) SDS] under shaking at 68° C. for 15 min. The membrane was removed and immersed again in washing solution 4 and shaken at 68° C. for 15 min. The signal detected on the membrane with DIG Luminescent Detection Kit (produced by Boehringer Mannheim) indicated that the DNA sequence derived from plasmid pT1 was inserted into the chromosome of Aspergillus oryzae TL+8 (pT1).

(4) Measurement of the activity of tannase from the transformant $1.2 \leq 10^5$ spores of the transformant Aspergillus oryzae TL+8 (pT1) were inoculated into 200 ml growth medium and cultured at 30° C. for 40 hours with stirring at 120 r.p.m. 2 g bacteria was obtained from the culture by filtration and cultured at 30° C. for 16 hours in 40 ml tannic acid liquid medium [2.5% (W/V) tannic acid, 5.3% (W/V) glucose, 1.2% (W/V) (NH$_4$)$_2$HPO$_4$, 0.2% (W/V) KH$_2$PO$_4$, 0.1% (W/V) MgSO$_4$, pH 6.8]. The culture was filtered and the filtrate was used as the enzyme solution. Separately, an enzyme solution was obtained from 1.2×10$^5$ spores of the parent strain Aspergillus oryzae TL-1 in the same manner as described above.

The enzyme solution was diluted 10 times (Aspergillus oryzae TL-1 strain) or 20 times [Aspergillus oryzae TL+8 (pT1) strain] with a citrate buffer (0.05M citric acid, pH 6.0). Then, 0.25 ml of the diluted enzyme solution was mixed with 1 ml reaction solution [0.35% (W/V) tannic acid, 0.05M citric acid, pH 6.0] previously heated at 30° C., and the mixture was incubated at 30° C. for 15 min. The reaction was terminated with 5 ml of 90% ethanol. Then, 0.25 ml of the reaction solution was diluted with 5 ml of 90% ethanol and the absorbance at 310 nm was measured. As the blank, the citrate buffer was used in place of the enzyme solution. Enzyme activity was calculated from the following equation. The results are shown in Table 1.

Enzyme activity (U/ml)=Δ310 nm×7.6×degree of dilution of sample Δ310 nm=blank absorbance−sample absorbance

TABLE 1

| | enzyme activity (U/ml) |
|---|---|
| Aspergillus oryzae TL-1 strain | 2.1 |
| Aspergillus oryzae TL+8 (pT1) strain | 15.9 |

What is claimed is:

1. A DNA fragment of 3,563 base pairs comprising a gene coding for tannase and derived from a microorganism belonging to the genus Aspergillus, with the following restriction enzyme map:

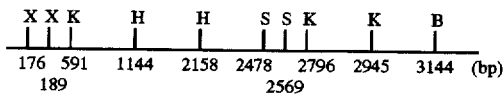

B: Bam HI, H: Hind III, K: Kpn I, S: Sal I, X: Xba I.

2. A DNA fragment according to claim 1, wherein the microorganism belonging to the genus Aspergillusis Aspergillus oryzae IAM 2636.

3. A DNA fragment comprising a tannase gene coding for an amino acid sequence represented by (SEQ ID NO:4).

4. A recombinant plasmid comprising a DNA fragment comprising a tannase gene as defined in claim 1, 2 or 3 inserted into a plasmid vector.

5. A process for producing tannase, comprising culturing a microorganism belonging to the genus Aspergillus, which has been transformed with the plasmid of claim 4, under conditions favorable to the expression of the gene encoding tannase, and recovering tannase from the culture.

6. A promoter represented by the nucleotide sequence of (SEQ ID NO:1).

* * * * *